United States Patent [19]

Perilhou et al.

[11] 4,270,546
[45] Jun. 2, 1981

[54] DEVICE FOR ULTRASONIC EXAMINATION OF BIOLOGICAL STRUCTURES

[75] Inventors: Jean R. Perilhou, Bourg-la-Reine; Roger H. Coursant, Paris, both of France

[73] Assignee: U.S. Philips Corporation, New York, N.Y.

[21] Appl. No.: 958,768

[22] Filed: Nov. 8, 1978

[30] Foreign Application Priority Data

Dec. 5, 1977 [FR] France ................. 77 36507

[51] Int. Cl.³ ............................. A61B 10/00
[52] U.S. Cl. ............................. 128/660; 73/602
[58] Field of Search ............... 128/660–663; 73/603, 607, 614, 618–626

[56] References Cited

U.S. PATENT DOCUMENTS

| | | | |
|---|---|---|---|
| 3,587,298 | 6/1971 | Jacobs | 73/607 |
| 3,676,584 | 7/1972 | Plakas et al. | 73/614 |
| 3,778,614 | 12/1973 | Hounsfield | 73/624 |
| 3,836,948 | 9/1974 | Burkhardt et al. | 340/1 R |
| 3,909,771 | 9/1975 | Pickering et al. | 73/620 |
| 3,918,024 | 11/1975 | Macovski | 73/614 |
| 4,011,750 | 3/1977 | Robinson | 73/628 |
| 4,026,144 | 5/1977 | Geriche et al. | 73/603 |
| 4,062,237 | 12/1977 | Fox | 128/663 |
| 4,109,642 | 8/1978 | Reid et al. | 73/622 |
| 4,137,775 | 2/1979 | LeMay | 128/660 |

OTHER PUBLICATIONS

Copenhaver, W. Metal, "Bailey's Textbook of Histology," 16th ed., Williams & Wilkins Co., Baltimore 1971, pp. 116–119, 207–209, 222.

Primary Examiner—Robert W. Michell
Assistant Examiner—Francis J. Jaworski
Attorney, Agent, or Firm—Thomas A. Briody; Robert T. Mayer; Jack E. Haken

[57] ABSTRACT

A device for determining preferred directions in biological structures by ultrasonic examination. The device comprises an electroacoustic converter which is subdivided into at least four sectors and which comprises transducers which are combined in groups in sectors which are diametrically situated with respect to the center. The transducers of each group are connected to the inputs of an adder. The outputs of the adders are connected to an arithmetic circuit which is adapted to form a first signal which is dependent of the sum of all signals generated by the transducers, and to form also a number of second signals which are dependent of the differences between signals generated by different transducer groups. The arithmetic circuit is connected to a display device for color images in a manner so that the first signals determines the brightness of the image, while the second signals determine the color information.

2 Claims, 3 Drawing Figures

DEVICE FOR ULTRASONIC EXAMINATION OF BIOLOGICAL STRUCTURES

The invention relates to a device for examination of biological structures by means of ultrasonic waves which are reflected by these structures. Specifically the invention comprises an electroacoustic converter which is subdivided into at least four sectors, each sector comprising at least one transducer.

An example of a system of this kind is described in U.S. Pat. No. 3,676,584.

A paper by Shuy et al, "Determination of Internal Properties by Spatial Echo Distribution Processing" relates tissue interface properties and spatial echo distribution for compensation of echo amplitudes in ultrasonic diagnostic imaging and may be found in Ultrasonics, September 1977, pp. 216–220.

The invention has for its object to provide a device which enables the characterization of preferred directions, for example, the situation of fibres 2, inside a biological structure.

To this end, the device in accordance with the invention is characterized in that transducers in sectors which are diametrically situated with respect to the center of the electroacoustic converter are combined to form groups, the transducers in each group being connected to the inputs of an adder, the outputs of said adders being connected to an arithmetic circuit which forms a first signal which is dependent on the sum of all signals generated by the transducer groups, and a number of second signals which are dependent on the differences between the signals generated by different transducer groups, said arithmetic circuit being connected to a display device for colour images in a manner so that the first signal determines the brightness of the image, while the second signals determine the colour information.

A preferred embodiment of the device in accordance with the invention is characterized in that the electroacoustic converter comprises both at least one annular zone which is sub-divided into sectors, each sector comprising at least one transducer, and a central zone which is not sub-divided The invention will be described in detail hereinafter with reference to the accompanying diagrammatic drawing.

Figure 1:
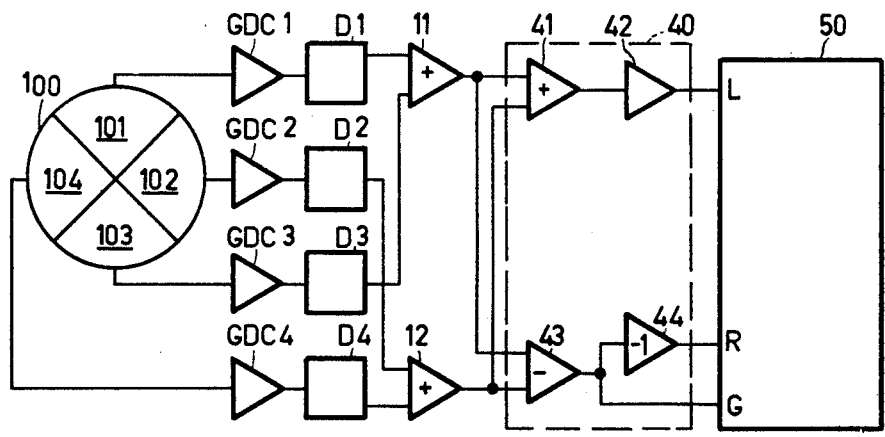
FIG. 1 shows a first embodiment of a device in accordance with the invention.

FIG. 1 shows a simple embodiment of a device in accordance with the invention whereby a distinction can be made between two orthogonal preferred directions. This device comprises an electroacoustic converter 100 which is subdivided into four sectors, each of which consists of a transducer, 101, 102, 103 and 104 respectively. The electrical signals supplied by each of these four transducers are applied to four amplifiers GDC1, GDC2, GDC3 and GDC4. These amplifiers are known per se and serve for the correction of the amplitude of the ultrasonic echo signals reflected to the electroacoustic device by the interfaces of the biological structures examined, as a function of the depth in these structures.

The output signals of the four amplifiers GDC1 to GDC4 are applied to four known detection circuits D1 to D4 in order to obtain envelope signals (or detected signals) of the signals supplied by the transducers.

The transducers in sectors which are diametrically situated with respect to the center of the electroacoustic converter 100 are combined to form groups (in this case pairs), each of the transducers associated with a pair being connected, via a network GDCi-Di, to the inputs of an adder. The transducers 101 and 103 are thus connected to an adder 11, and the transducers 102 and 104 are connected to an adder 12. These known adders comprise operational amplifiers.

The outputs of the adders 11 and 12 are connected to an arithmetic circuit 40. This arithmetic circuit comprises an adder 41 which sums the output signals of the adders 11 and 12, thus forming a first signal which is applied as a brightness signal L, via an amplifier 42, to a device 50 for the display of colour images (known per se). The arithmetic circuit 40 furthermore comprises a subtraction device 43 (differential amplifier) which forms a second signal which represents the difference between the output signals of the adders 11 and 12. This second signal is applied to the display device 50 on the one hand directly as the "green" signal G, and on the other hand, via an inverter circuit 44, as the "red" signal R.

The operation of the described device may be described as follows. When the biological structure examined is anisotropic and comprises, for example, fibres which are situated mainly parallel to the direction which is determined approximately by the transducer 101, 103 (bisector of the sectors 101 and 103), the echo signals intercepted by the transducers 101 and 103 have an amplitude which is higher than that of the signals intercepted by the transducers 102 and 104. The occurrence of a difference in amplitude between said echo signals will become manifest on the output of the subtraction circuit 43, and will give rise to the appearance of an intense colour at the location in the displayed ultrasonic image displayed by the display device which corresponds to these fibres. The green colour will correspond to the direction 101–103, while the red colour (the inverse of the preceding difference signal) will correspond to the direction 102–104.

When the biological structure examined is isotropic, the ultrasonic echo signals are isotropically distributed between all sectors, and a yellow colour will be obtained in the image displayed.

Figure 2:
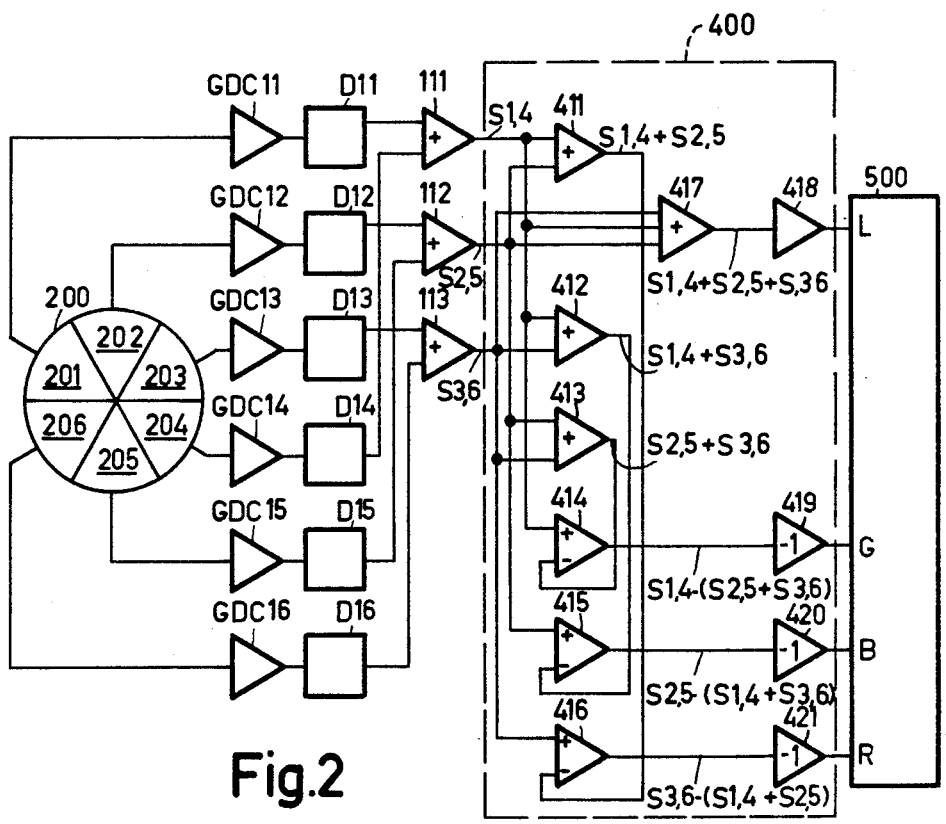
FIG. 2 shows a second embodiment of a device in accordance with the invention.

FIG. 2 shows a more refined embodiment of the device in accordance with the invention. The electroacoustic converter 200 in this case comprises six sectors of transducers which are denoted by the reference numerals 201–206. Thanks to these six sectors, a higher accuracy can be realised for the determination of the preferred directions. A distinction can now be made between two preferred directions which deviate 60°, from each other.

Like in the embodiment shown in FIG. 1, the electrical signals supplied by each of the six sectors 201 to 206 of the electroacoustic converter 200 are suitably corrected as regards amplitude, after which they are detected by means of relevant amplifiers GDC11 to GDC16 and detection circuits D11 to D16, respectively.

Subsequently, the signals thus obtained are added two by two in that each time the transducers in two diametrically situated sectors with respect to the center form a group and are connected to an adder. For this purpose, the transducers of the sectors 201 and 204 are connected to an adder 111, those of the sectors 202 and 205 to an adder 112, and those of the sectors 203 and 206 to an adder 113. The output signals of these adders are denoted by the references S1,4, S1,5 and S3,6, respectively.

These signals are applied to an arithmetic circuit 400 which inter alia comprises three adders 411, 412 and 413 in order to form relevant sum signals S1,4+S2,5, S1,4+S3,6, and S2,5+S3,6, and a fourth adder 417 in order to form a first signal S1,4+S2,5+S3,6. The arithmetic circuit 400 furthermore comprises three subtraction devices (differential amplifiers) 414, 415 and 416. The "plus" input of each of these subtraction devices is connected to the ouput of one of the adders 111, 112 and 113, and the "minus" input thereof is connected to the output of one of the adders 411, 412 and 413, the arrangement being such that the second signals S1,4−(S2,5+S3,6), S2,5−(S1,4+S3,6) and S3,6−(S1,4+S2,5) are formed on the outputs of the subtraction devices 414, 415 and 416, respectively.

The first signal S1,4+S2,5+S3,6 is applied as a brightness signal L, via an amplifier 418, to a device 500 for the display of colour images, and the second signals are applied thereto, via the inversion circuits 419, 420 and 421, as the "green" signal G, the "blue" signal B, and the "red" signal R, respectively.

The brightness of the image displayed is thus determined by the sum of the output signals of all transducer groups, and the colour information is determined by the differences between these output signals.

The operation of the described second embodiment corresponds to that described with reference to FIG. 1. The only difference consists in that the number of difference signals to be formed: in this case three difference signals.

Figure 3:
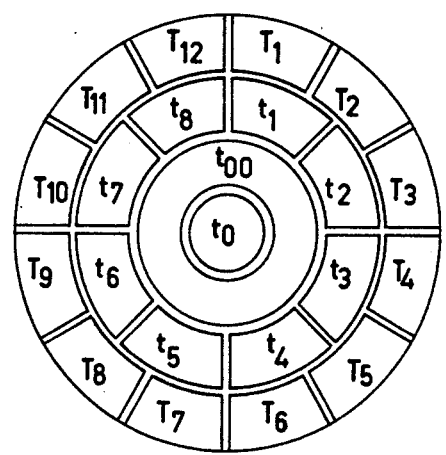
FIG. 3 shows an embodiment of an electroacoustic converter for a device in accordance with the invention.

FIG. 3 shows a preferred embodiment of an electroacoustic converter comprising transducers. This device comprises a first central zone $t_o$ which is not sub-divided and which consists of one transducer which is generally used for transmitting ultrasonic pulses to the biological structure examined. A second (annular) zone $t_{oo}$ which surrounds the central zone can be used for the same purpose, and also serves for intercepting the echo signals.

Said converter, moreover, comprises a third zone which also has an annular shape and which is formed by eight identical transducers $t_1, t_2, \ldots t_8$. Finally, a fourth annular zone is formed by 12 identical transducers $T_1$ to $T_{12}$. This electroacoustic converter thus comprises four sectors (quadrants), each of which comprises three transducers from the fourth zone and two transducers from the third zone. The transducers are made of, for example, a known piezo ceramic material.

When use is made of the electroacoustic device described with reference to FIG. 3, the directional effect can be intensified, or given directions may be favoured by additional amplification of the output signal of given transducers before it is applied to the correction amplifiers GDC.

For example, when the signals supplied by the transducers of the fourth zone are amplified more than the signals supplied by the transducers of the third zone which are amplified more again than the signals produced by the transducers of the second zone, the directional effect is intensified. Furthermore, for example, preference can be given to the transducers $T_1$, $T_7$ and $T_4$, $T_{10}$ which form part of the fourth zone, in order to favour two orthogonal preferred directions. To this end, the signals of these transducers are additionally amplified.

What is claimed is:

1. A device for examining biological structures by means of ultrasonic waves which are reflected by those structures, comprising:
   an electroacoustic converter, said converter comprising at least four transducers, at least some of said transducers being grouped into pairs, each pair consisting of transducers which are diametrically situated with respect to the center of the converter;
   a plurality of adders, each adder being connected to sum output signals from one pair of transducers;
   arithmetic circuit means, connected to receive output signals from said adders, which function to form a first signal representative of the sum of the signals produced by all of the transducers pair and a number of second signals which are representative of the difference between the signals generated by different transducer pairs or groups of pairs; and
   display means connected to receive the first and second signals from the arithmetic circuit and to display images such that the first signal determines the brightness of points in the image and the second signals determine color information at points in the image, whereby the image is a characterization on tissue types in the biological structures.

2. A device as claimed in claim 1 wherein the electroacoustic converter comprises a single central transducer and an annular zone which surrounds the central transducer and is subdivided into sectors, each sector comprising at least one transducer.

* * * * *